United States Patent [19]
> Obase et al.

[11] 4,147,799
[45] Apr. 3, 1979

[54] PROCESS FOR REDUCING BLOOD PRESSURE AND BLOCKING β-ADRENERGIC RECEPTOR

[75] Inventors: Hiroyuki Obase, Sakai; Yutaka Kasuya, Kawasaki, both of Japan

[73] Assignee: Kyowa Hakko Kogyo Co., Ltd., Tokyo, Japan

[21] Appl. No.: 463,833

[22] Filed: Apr. 24, 1974

Related U.S. Application Data

[63] Continuation of Ser. No. 264,336, Jun. 19, 1972, abandoned.

[30] Foreign Application Priority Data

Jun. 24, 1971 [JP] Japan .................................. 46-45206
Jun. 24, 1971 [JP] Japan .................................. 46-45207
Jun. 30, 1971 [JP] Japan .................................. 46-47148

[51] Int. Cl.$^2$ .............................................. A61K 31/36
[52] U.S. Cl. ............................. 424/282; 260/340.5 R
[58] Field of Search ..................... 424/282; 260/340.5

[56] References Cited

U.S. PATENT DOCUMENTS

| | | | |
|---|---|---|---|
| 1,073,966 | 9/1913 | Decker | 260/340.5 |
| 1,964,973 | 7/1934 | Bockmuhl et al. | 260/340.5 |
| 2,011,454 | 8/1935 | Nagai | 260/340.5 |
| 3,657,244 | 4/1972 | Mentrup et al. | 260/340.5 |

*Primary Examiner*—Anna P. Fagelson
*Attorney, Agent, or Firm*—Fitzpatrick, Cella, Harper & Scinto

[57] ABSTRACT

Ethanolamine derivatives and their acid addition salts are prepared (1) by reacting a 1-(3,4-methylenedioxyphenyl)-2-aminoethanol compound or an α-amino-(3,4-methylenedioxy)acetophenone compound with an alkanal or an alkanone under reduction conditions, (2) by hydrogenating and/or hydrogenolyzing a 1-(3,4-methylenedioxyphenyl)-2-(N-substituted amino)-ethanol compound or an α-(N-substituted amino)-(3,4-methylenedioxy)acetophenone compound, and (3) by reacting a (3,4-methylenedioxyphenyl)-ethylene oxide compound or a 1-(3,4-methylenedioxyphenyl)-2-substituted ethanol compound with an amine. The ethanolamine derivatives and their salts show β-adrenergic receptor blocking activity, and are expected to be useful in the treatment of heart disease, hypertension, myocardites and pheochromocytoma.

8 Claims, 6 Drawing Figures

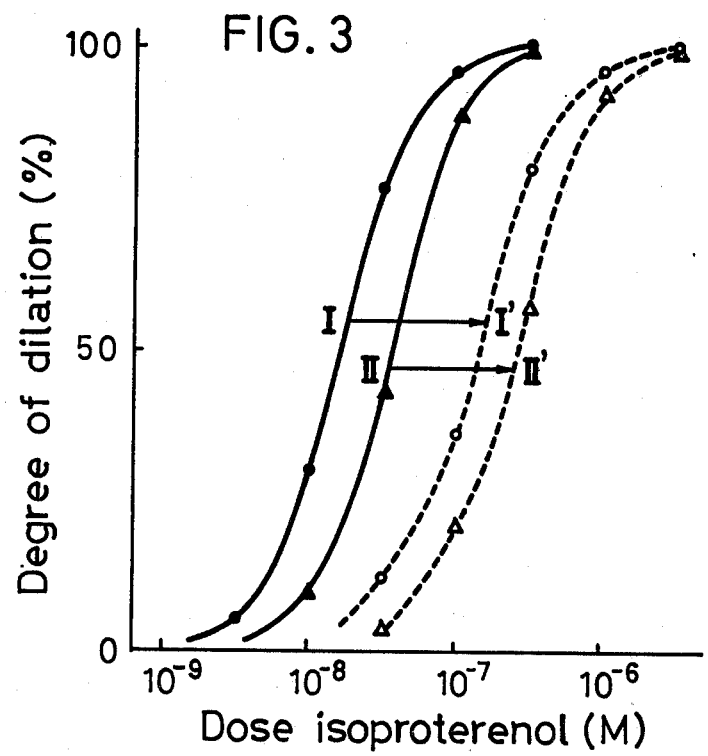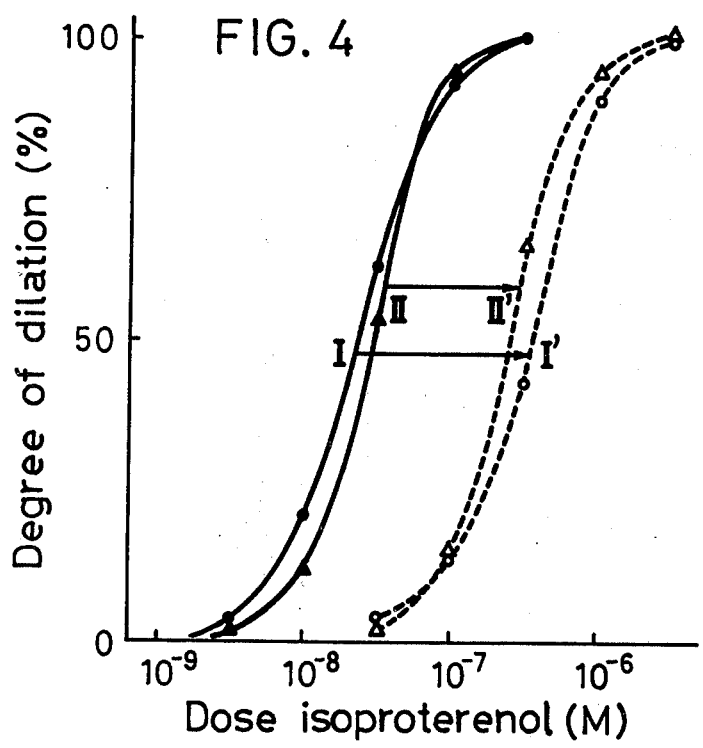

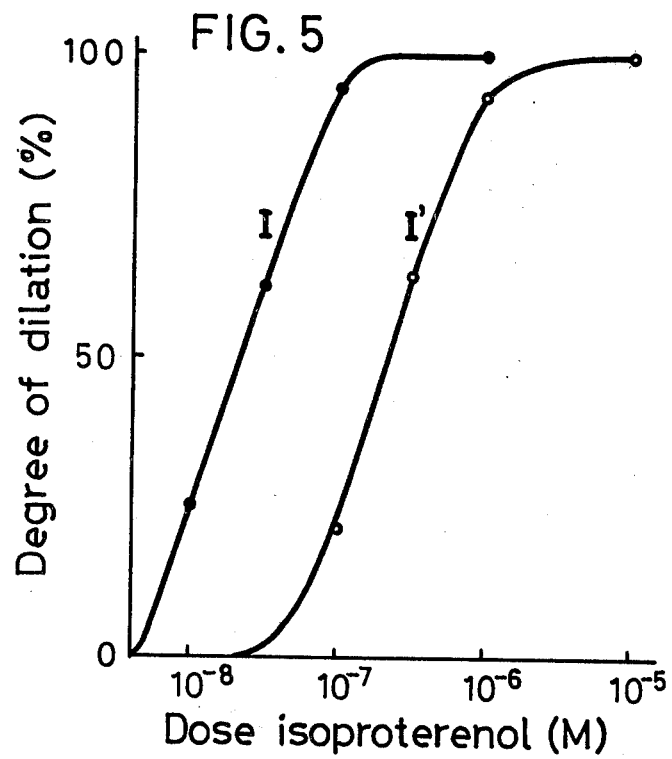
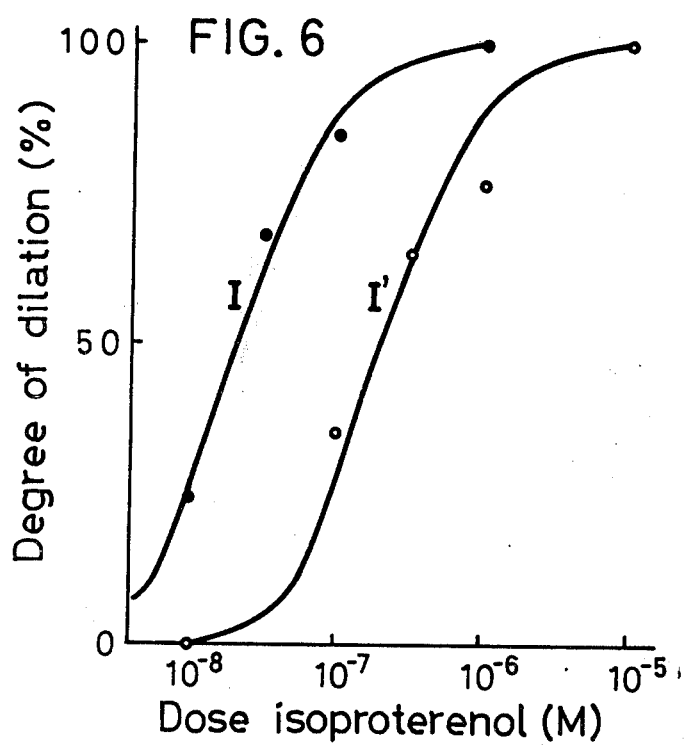

PROCESS FOR REDUCING BLOOD PRESSURE AND BLOCKING β-ADRENERGIC RECEPTOR

This is a continuation, of application Ser. No. 264,336, filed June 19, 1972, and now abandoned.

BACKGROUND OF THE INVENTION

This invention relates to ethanolamine derivatives and acid addition salts thereof. More specifically, this invention relates to 1-(3,4-methylenedioxyphenyl)-2-alkylaminoethanol compounds and to methods for preparing same. The ethanolamine derivatives and their salts show strong pharmacological activity, especially β-adrenergic receptor blocking activity. The compounds are, therefore, expected to be useful in the treatment or prevention of nervous disorders such as heart disease, hypertension, myocardites and pheochromocytoma.

The compounds which are the subject of the present invention are 1-(3,4-methylenedioxyphenyl)-2-alkylaminoethanol compounds and are represented by the formula

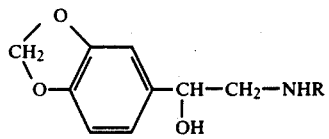

wherein R represents a straight or branched chain alkyl group having 2 to 6 carbon atoms, such as an ethyl, n-propyl, isopropyl, n-butyl, sec-butyl, n-amyl, isoamyl or n-hexyl group.

The 1-(3,4-methylenedioxyphenyl)-2-alkylaminoethanol compounds may be employed in the form of the free amine, or in the form of a salt. Suitable salts are the acid addition salts such as, for example, the salts of inorganic acids such as the hydrochloride, hydrobromide, phosphate and sulfate, the organic acid salts such as the oxalate, lactate, tartrate, naphthoate, acetate, salicylate, citrate, benzoate, adipate and maleate. The relatively insoluble salts such as 1,1'-methylene-bis-(2-hydroxy-3-naphthoate) are particularly useful since its physical properties enable it to remain in the blood at a constant level. Salts prepared from an acidic synthetic resin, such as the salts of a sulfonated polystyrene resin, may also be employed. The sulfonated polystyrene resin sold under the trademark ZEO-KARB 225 from The Permutit Co., Ltd., Great Britain is an example of a suitable synthetic resin.

DESCRIPTION OF THE PREFERRED EMBODIMENTS

Figure 1:
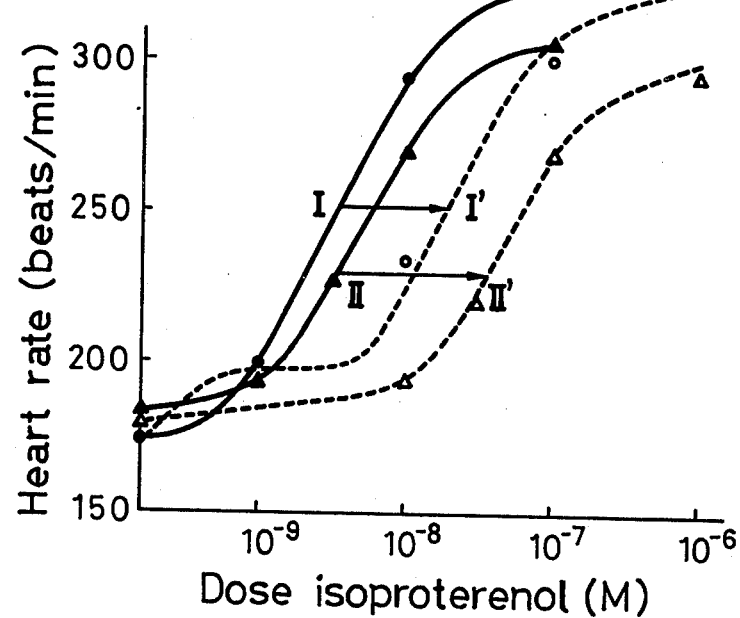

The 1-(3,4-methylenedioxyphenyl)-2-alkylaminoethanol compounds can be prepared by reacting a compound represented by the formula

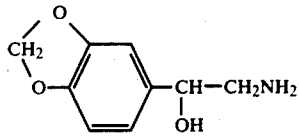

[1-(3,4-methylenedioxyphenyl)-2-aminoethanol] or

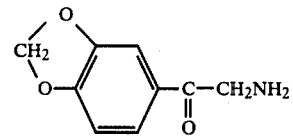

[α-amino-(3,4-methylenedioxy)acetophenone] with a lower alkanal or a lower alkanone having 2 to 6 carbon atoms under reduction conditions. Lower alkanals such as acetaldehyde, propionaldehyde, butyraldehyde, isobutyraldehyde, n-amylaldehyde, isoamylaldehyde and n-hexylaldehyde may be employed. Lower alkanones such as acetone, methyl ethyl ketone, methyl n-propyl ketone, diethyl ketone and hexanone-2 may be employed. The reaction can be carried out under atmospheric pressure or under applied pressure with heating and stirring in the presence of hydrogen and a suitable catalyst. Alternatively, the reaction can be carried out in the presence of such reducing agents as lithium aluminum hydride, sodium borohydride, potassium borohydride, and the like. Catalysts generally employed in hydrogenation reactions such as, for example, platinum, palladium-carbon and Raney nickel, may be employed. The reaction is generally carried out in an inert diluent or solvent such as methanol, ethanol, isopropyl alcohol, dioxane and the like. Generally, the reaction is allowed to proceed until the theoretical amount of hydrogen is absorbed. The reaction is carried out at a temperature between 20 and 50° C. The 1-(3,4-methylenedioxyphenyl)-2-alkylaminoethanol compound is collected from the reaction mixture and purified by techniques known in the art.

The 1-(3,4-methylenedioxyphenyl)-2-alkylaminoethanol compounds can also be prepared by hydrogenating and/or hydrogenolyzing a compound represented by the formula

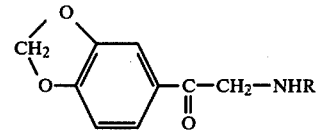

[α-alkylamino-(3,4-methylenedioxy)acetophenone]

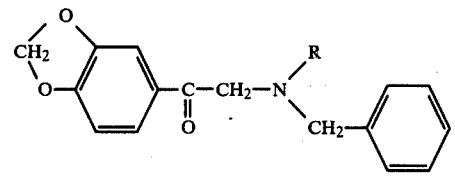

[α-alkylbenzylamino-(3,4-methylenedioxy)acetophenone]

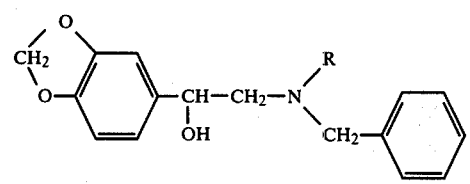

[1-(3,4-methylenedioxyyphenyl)-2-alkylbenzylaminoethanol] wherein R is a straight or branched chain lower alkyl group having 2–6 carbon atoms, in the presence of a noble metal catalyst such as a palladium-carbon catalyst or a nickel or nickel alloy catalyst such as Raney nickel, in a suitable organic solvent. The reaction can be carried out at room temperature or with heating under atmospheric pressure or under applied pressure. Any solvent usually used in catalytic reduction reactions such as methanol, ethanol, isopropyl alcohol and the like can be employed. Where the reaction is carried out at elevated temperatures, usually a temperature between 60–130° C. is employed. The reaction is generally carried out until the theoretical amount of hydrogen has been absorbed. The 1-(3,4-methylenedioxyphenyl)-2-alkylaminoethanol compound is collected and purified by techniques known in the art.

Alternatively, the 1-(3,4-methylenedioxyphenyl)-2-alkylaminoethanol compounds can be prepared by reacting a compound represented by the formula

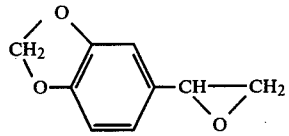

(III)$_a$

[(3,4-methylenedioxyphenyl)ethylene oxide] or

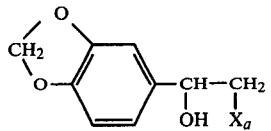

(III)$_b$

[1-(3,4-methylenedioxyphenyl)-2-substituted ethanol] wherein X$_a$ is a halogen atom such as chlorine, bromine or iodine, a leaving group such as

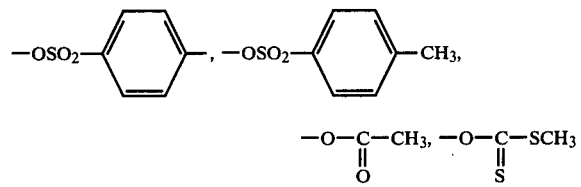

and the like, with an amine represented by the formula, H$_2$HR, wherein R is a straight or branched chain lower alkyl group having 2 to 6 carbon atoms.

The reaction can be carried out in the presence or absence of a solvent. Where a solvent is employed, organic solvents such as benzene, toluene, ethanol, chloroform, and the like may be employed. In general, any solvent that does not participate in the reaction may be employed. Where a solvent is employed, the reaction is generally carried out at the reflux temperature of the particular solvent employed. Where the reaction is carried out in the absence of a solvent, the reactants are heated at a temperature between 50 and 130° C. The dry reaction is preferably carried out in an autoclave with heating.

The salts of the 1-(3,4-methylenedioxyphenyl)-2-alkylaminoethanol compounds can be prepared by the usual techniques used to prepare acid addition salts of amines. Where the starting compound is already in the form of an acid addition salt, the 1-(3,4-methylenedioxyphenyl)-2-alkylaminoethanol compound is obtained in the form of the corresponding acid salt.

The 1-(3,4-methylenedioxyphenyl)-2-aminoethanol compounds (I)$_a$ used as the starting material can be prepared by reducing a compound represented by the formula

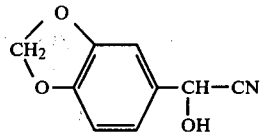

[(3,4-methylenedioxyphenyl)cyanocarbinol] in ether with lithium aluminum hydride [J. Ind. Chem., 36, 585 (1959)]. The starting material can also be obtained by reducing a compound of the formula

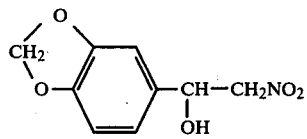

[1-(3,4-methylenedioxyphenyl)-2-nitroethanol] according to the process described in J. Org. Chem., 21, 1228 (1956). The 1-(3,4-methylenedioxyphenyl)-2-nitroethanol compound is obtained by reacting (3,4-methylenedioxy)benzaldehyde with nitromethane in the presence of a suitable catalyst such as a nickel alloy catalyst or a palladium-carbon catalyst.

Where the α-amino-(3,4-methylenedioxy)acetophenone compounds (I)$_b$ are used as the starting material, the compounds can be prepared according to the process described in Arch. Pharm. 269, 581 (1931).

The α-alkylamino-(3,4-methylenedioxy)acetophenone compounds (II)$_a$ and α-alkylobenzylamino-(3,4-methylenedioxy)-acetophenone compounds (II)$_b$ used as the starting materials in the preparation of the 1-(3,4-methylenedioxyphenyl)-2-alkylaminoethanol compounds can be prepared by reacting a compound of the formula

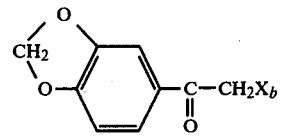

[α-substituted-(3,4-methylenedioxy)acetophenone] wherein X$_b$ is a halogen atom with the corresponding amine represented by the formula:

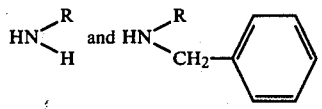

wherein R is a straight or branched chain lower alkyl group hving 2–6 carbon atoms. Chlorine and bromine are suitable halogens. The reaction can be carried out at a temperature ranging from 0° to 5° C. in a suitable solvent. Inert solvents such as ethyl acetate, benzene, acetone, and the like may be employed, but any solvent that does not participate in the reaction may be used.

The α-alkylamino-(3,4-methylenedioxy)acetophenone compounds (II)$_a$ and the α-alkylbenzylamino-(3,4-methylenedioxy)acetoxyphenone compounds (II)$_b$ can also be prepared by reacting the corresponding compounds of the general formula

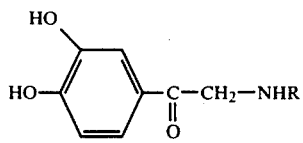

[4-(alkylaminoacetyl)catechol]
or

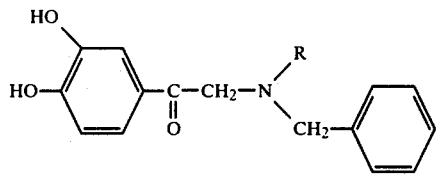

[4-(alkylbenzylaminoacetyl)catechol] wherein R is a straight or branched chain lower alkyl group having 2–6 carbon atoms with a compound of the formula X—CH₂X wherein X is a halogen atom, in the presence of a suitable catalyst. Chlorine, bromine and iodine are suitable halogens. As the catalyst, an alkali such as, for example, potassium hydroxide, sodium hydroxide, potassium bicarbonate and sodium bicarbonate, or Tobin bronze shavings (consisting of 60% Cu, 38% Zn, 1.5% Sn., 0.2% Fe and 0.3% PbO) may be employed.

The above formulated 4-(alkylaminoacetyl)catechol compounds and 4-(alkylbenzylaminoacetyl)catechol compounds can be prepared by reacting a compound of the formula

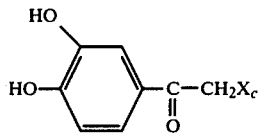

[4-(haloacetyl)cathecol]
wherein $X_c$ represents a halogen atom with a compound of the formula

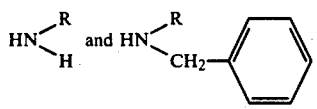

wherein R is a straight or branched chain lower alkyl group having 2–6 carbon atoms. As the halogen, chlorine and bromine are suitable. The reaction can be carried out at low temperature ranging from 0° to 5° C. using a suitable solvent such as ethyl acetate, benzene, acetone and the like. Any inert solvent that does not participate in the reaction may be used.

The 1-(3,4-methylenedioxyphenyl)-2-alkylbenzylaminoethanol compounds (II)$_c$ can be prepared by reacting a compound of the formula

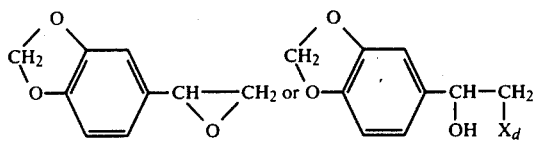

with a compound of the formula

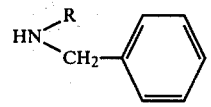

wherein R is a lower alkyl group having 2–6 carbon atoms, and $X_d$ is a halogen such as chlorine or bromine.

The dry reactants can be reacted together or the reaction can be carried out in a suitable solvent. Solvents such as benzene, toluene, ethanol, chloroform, and the like may be employed, but any solvent that does not participate in the reaction can be used. In carrying out the reaction, the reaction temperature is not specifically limited, but is suitably selected depending upon the reflux temperature of the solvent. When a solvent is not used, the reaction is carried out with heating at a temperature of 50° to 130° C. When heat is employed to effect the reaction, the reaction is preferably carried out in an autoclave.

Now, the present invention will be further explained, referring to the following examples, but these examples are merely illustrative and do not restrict the scope of the present invention.

EXAMPLE 1

1-(3,4-METHYLENEDIOXYPHENYL)-2-ISOPROPYLAMINOETHANOL 18.1 g. of 1-(3,4-methylenedioxyphenyl)-2-aminoethanol hydrochloride are dissolved in 20 ml. of acetone and 300 ml. of ethanol. To the resulting solution are added 10 g. of extended Raney nickel and the mixture is heated and stirred at 70° C. in an atmosphere of hydrogen in an autoclave. After the absorption of hydrogen is complete, the catalyst is filtered off and the filtrate is concentrated to dryness. Upon recrystallization of the crude crystalline residue from isopropyl alcohol, 14.4 g. of 1-(3,4-methylenedioxyphenyl)-2-isopropylaminoethanol hydrochloride are obtained as white needles.

Melting point: 182°–182.5° C. Elementary analysis: as $C_{12}H_{17}NO_3 \cdot HCL$; Calculated: C=55.49, H=6.99, N=5.39; Found: C=55.38, H=6.78, N=5.51.

5 g. of 1-(3,4-methylenedioxyphenyl)-2-isopropylaminoethanol hydrochloride are dissolved in 20 mol. of water, and the resulting aqueous solution is made basic with 1N caustic soda. The liberated oil is extracted with ether. The ether layer is separated and dried and the ether is removed by distillation. Upon recrystallization of the crystalline residue from petroleum ether, 1-(3,4-methylenedioxyphenyl)-2-isopropylaminoethanol is obtained as white needle crystals having a melting point of 117°–118° C.

EXAMPLE 2

1-(3,4-METHYLENEDIOXYPHENYL)-2-ISOPROPYLAMINOETHANOL HYDROCHLORIDE 2 g. of extended Raney nickel are added to a solution of 17.9 g. of α-amino-(3,4-methylenedioxy)acetophenone, 50 ml. of acetone and 100 ml. of ethanol, and the resulting mixture is hydrogenated with vigorous stirring at a reaction temperature of 50° C. and a reaction pressure of 50 atmospheres. After the absorption of hydrogen is complete, the catalyst is filtered off, and the filtrate is concentrated under a reduced pressure to dryness. The crude crystalline residue is dissolved in ethyl acetate and ethyl acetate acidified with hydrochloric acid is added to the solution until the white turbidity ceases to form. The crystals which form on standing are filtered off and washed with ethyl acetate. Upon recrystallization from isopropyl alcohol, 22.3 g. of 1-(3,4-methylenedioxyphenyl)-2-isopropylaminoethanol hydrochloride are obtained.

Melting point: 182°–182.7° C. Elementary analysis: as $C_{12}H_{17}NO_3 \cdot HCl$; Caliculated: C=55.49, H=6.99, N=5.39; Found: C=55.39, H=6.98, N=5.42.

EXAMPLE 3

1-(3,4-METHYLENEDIOXYPHENYL)-2-ISOPROPYLAMINOETHANOL HYDROCHLORIDE 6.5 g. of α-isopropylamino-(3,4-methylenedioxy)-acetophenone hydrochloride are dissolved in 300 ml. of methanol and to the solution are added with stirring 2 g. of palladium-carbon. The resulting mixture is hydrogenated with vigorous stirring under atmospheric pressure. After about 2 hours, the theoretical amount of hydrogen is absorbed. The catalyst is filtered off and upon concentrating the filtrate, 7.5 g. of crude crystals are obtained. Upon recrystallization of the crude crystals from isopropyl alcohol, 5 g. of 1-(3,4-methylenedioxyphenyl)-2-isopropylaminoethanol hydrochloride are obtained as white crystalline needles having a melting point of 182°–182.7° C.

The crystals are dissolved in 20 ml. of water and the resulting aqueous solution is made basic with an aqueous saturated solution of sodium hydrogen carbonate. The liberated oil is extracted with ether. The resulting ether layer is separated and dried and the ether is removed by distillation. Upon recrystallization of the residual crystals from petroleum ether, 1-(3,4-methylenedioxyphenyl)-2-isopropylaminoethanol is obtained as white crystalline needles having a melting point of 117°–118° C.

Elementary analysis: as $C_{12}H_{17}NO_3 \cdot HCl$; Calculated: C=55.49, H=6.99, N=5.39; Found: C=55.56, H=7.25, N=5.36.

EXAMPLE 4

1-(3,4-METHYLENEDIOXYPHENYL)-2-ISOPROPYLAMINOETHANOL HYDROCHLORIDE 52.5 g. of α-isopropylbenzylamino-(3,4-methylenedioxy)acetophenone hydrochloride are dissolved in 2 l. of methanol and to the solution are added with stirring 1 g. of palladium-carbon. The resulting mixture is hydrogenated and hydrogenolyzed simultaneously with vigorous stirring under atmospheric pressure. After about 5 hours, the theoretical amount of hydrogen is absorbed. The catalyst is filtered off and upon concentrating the filtrate, 31 g. of the crude crystals are obtained. Upon recrystallization of the crude crystals from isopropyl alcohol, 25 g. of 1-(3,4-methylenedioxyphenyl)-2-isopropylaminoethanol hydrochloride are obtained as white crystaline needles having melting point of 182°–182.7° C.

Elementary analysis: as $C_{12}H_{17}NO_3 \cdot HCl$; Calculated: C=55.49, H=6.99, N=5.39; Found: C=55.53, H=7.21, N=5.38.

EXAMPLE 5

1-(3,4-METHYLENEDIOXYPHENYL)-2-ISOPROPYLAMINOETHANOL HYDROCHLORIDE 35 g. of 1-(3,4-methylenedioxyphenyl)-2-isopropylbenzylaminoethanol hydrochloride are dissolved in 1 liter of methanol with stirring. To the resulting solution are added 3 g. of palladium carbon and the mixture is hydrogenolyzed with vigorous stirring at room temperature under atmospheric pressure. After the theoretical amount of hydrogen is absorbed, the stirring is stopped and the reaction solution is filtered. Upon removal of the solvent by distillation under reduced pressure, 23 g. of crude crystals are obtained. Upon recrystallization of the crude crystals from isopropyl alcohol, 22.5 g. of 1-(3,4-methylenedioxyphenyl)-2-isopropylaminoethanol hydrochloride are obtained as white needles.

Melting point: 182°–182.5° C. Elementary analysis: as $C_{12}H_{17}NO_3 \cdot HCl$; Calculated: C=55.49, H=6.99, N=5.39; Found: C=55.63, H=6.72, N=5.37.

EXAMPLE 6

1-(3,4-METHYLENEDIOXYPHENYL)-2-ISOPROPYLAMINOETHANOL HYDROCHLORIDE

A solution of 16.4 g. of (3,4-methylenedioxyphenyl)-ethylene oxide, 150 g. of isopropylamine in 100 ml. of ethanol is mildly refluxed for 6 hours. After cooling, the ethanol and excess amine are distilled off under reduced pressure. The residue is extracted with 100 ml. of 1N HCl and the extract is washed twice with 50 ml. of ether. The hydrochloric acid extract solution is made basic with 1N caustic soda, and the liberated oil is extracted with ether. The ether extract is dried and an etherial hydrochloric acid solution is added thereto. The crystalline hydrochloride settles out of solution and is filtered and dried to yield 8.7 g. of crude product. Upon recrystallization from isopropyl alcohol, 8.1 g. of 1-(3,4-methylenedioxyphenyl)-2-isopropylaminoethanol hydrochloride are obtained.

Melting point: 182°–182.7° C. Elementary analysis: as $C_{12}H_{17}NO_3 \cdot HCl$; Calculated: C=55.49, H=6.99, N=5.39; Found: C=55.43, H=6.87, N=5.53.

5 g. of 1-(3,4-methylenedioxyphenyl)-2-isopropylaminoethanol hydrochloride are dissolved in 20 ml. of water and the resulting aqueous solution is made basic with 1N caustic soda. The liberated oil is extracted with ether and the ether layer is separated and dried. The ether is then removed by distillation. Upon recrystallization of the residual crystals from petroleum ether, 1-(3,4-methyllenedioxyphenyl)-2-isopropylaminoethanol is obtained as white crystalline needles having a melting point of 117°–118° C.

EXAMPLE 7

1-(3,4-METHYLENEDIOXYPHENYL)-2-ISOPROPYLAMINOETHANOL HYDROCHLORIDE 20.5 g. of 1-(3,4-methylenedioxyphenyl)-2-chloroethanol are mixed with 30 g. of isopropylamine and 100 ml. of ethanol and the mixture is refluxed for 8 hours. After cooling, the ethanol and excess amine are removed by distillation under reduced pressure. The residue is extracted with 100 ml. of 1N HCl and the extract is washed twice with 50 ml. of ether. The hydrochloric acid extract is made basic with 1N caustic soda, and the liberated oil is extracted with ether. The ether extract is dried and an etherial hydrochloric acid solution is added. The crystalline hydrochloride settles out of solution and is filtered and dried. Upon recrystallization of the crude crystals from isopropyl alcohol, 6.4 g. of 1-(3,4-methylenedioxyphenyl)-2-isopropylaminoethanol hydrochloride are obtained.

Melting point: 182°–182.7° C. Elementary analysis: as $C_{12}H_{17}NO_3 \cdot HCl$; Calculated: C=55.49, H=6.99, N=5.39; Found: C=55.62, H=7.01, N=5.38.

EXAMPLE 8

1-(3,4-METHYLENEDIOXYPHENYL)-2-ETHYLAMINOETHANOL HYDROCHLORIDE 18 g. of 1-(3,4-methylenedioxyphenyl)-2-aminoethanol hydrochloride are dissolved in 300 ml. of ethanol and 50 ml. of 80% aqueous solution of acetaldehyde. To the resulting solution are added 0.5 g. of extended Raney nickel and the mixture is heated at 70° C. in an atmosphere of hydrogen in a 1 liter-autoclave. After the absorption of hydrogen is complete, the mixture is cooled. Then the catalyst is filtered off and the filtrate is concentrated to dryness. Upon recrystallization of the crude crystalline residue from isopropyl alcohol, 12.5 g. of 1-(3,4-methylenedioxyphenyl)-2-ethylaminoethanol hydrochloride are obtained as white needles.

Elementary analysis: as $C_{11}H_{15}NO_3.HCl$; Calculated: C=53.77, H=6.56, N=5.70; Found: C=53.82, H=6.62, N=5.71.

EXAMPLE 9

1-(3,4-METHYLENEDIOXYPHENYL)-2-ETHYLAMINOETHANOL HYDROCHLORIDE 19.5 g. of 1-(3,4-methylenedioxyphenyl)-2-chloroethanol are added to a solution of 170 g. of ethylamine in 200 ml. of cooled ethanol and the mixture is heated at 80° C. for 8 hours in an autoclave. After cooling, the ethanol and excess ethylamine are distilled off under reduced pressure. The residue is extracted with 100 ml. of 1N HCl and the extract is washed twice with 100 ml. of ether. The hydrochloric acid extract solution is made basic with 1N caustic soda and the liberated oil is extracted with ether. The ether extract is dried and an etherial hydrochloric acid solution is added thereto. The crystals which settle out on standing are filtered off and washed with ether. Upon recrystallization from isopropyl alcohol 7.8 g. of 1-(3,4-methylenedioxyphenyl)-2-ethylaminoethanol hydrochloride are obtained.

Elementary analysis: as $C_{11}H_{15}NO_3.HCl$; Calculated: C=53.77, H=6.56, N=5.70; Found: C=53.68, H=6.43, N=5.77.

EXAMPLE 10

1-(3,4-METHYLENEDIOXYPHENYL)-2-t-BUTYLAMINOETHANOL HYDROCHLORIDE

The procedure described in Example 5 is repeated except that 38 g. of 1-(3,4-methylenedioxyphenyl)-2-t-butylbenzylaminoethanol hydrochloride are used in place of the 1-(3,4-methylenedioxyphenyl)-2-(isopropylbenzylaminoethanol hydrochloride. 23.9 g. 1-(3,4-methylenedioxyphenyl)-2-t-butylaminoethanol hydrochloride are obtained.

Elementary analysis: as $C_{13}H_{19}NO_3.HCl$; Calculated: C=57.04, H=7.36, N=5.12; Found: C=57.41, H=7.29, N=4.87.

EXAMPLE 11

1-(3,4-METHYLENEDIOXYPHENYL)-2-t-BUTYLAMINOETHANOL HYDROCHLORIDE

The procedure described in Example 4 is repeated except that 72 g. of α-(t-butylbenzylamino)-(3,4-methylenedioxy)acetophenone hydrochloride are used in place of the α-isopropylbenzylamino-(3,4-methylenedioxy)acetophenone hydrochloride. 47.3 g. of 1-(3,4-methylenedioxyphenyl)-2-t-butylaminoethanol hydrochloride are obtained as white crystalline needles.

Elementary analysis: as $C_{13}H_{19}NO_3.HCl$; Calculated: C=57.04, H=7.36, N=5.12; Found: C=57.01, H=7.48, N=4.97.

EXAMPLE 12

1-(3,4-METHYLENEDIOXYPHENYL)-2-t-BUTYLAMINOETHANOL HYDROCHLORIDE

The procedure described in Example 6 is repeated except that 186 g. of t-butylamine are used in place of the isopropylamine. 8.5 g. of 1-(3,4-methylenedioxyphenyl)-2-t-butylaminoethanol hydrochloride are obtained.

Elementary analysis: as $C_{13}H_{19}NO_3.HCl$; Calculated: C=57.04, H=7.36, N=5.12; Found: C=56.86, H=7.38, N=5.31.

PREPARATION OF STARTING MATERIALS

EXAMPLE A

1-(3,4-METHYLENEDIOXYPHENYL)-2-AMINOETHANOL HYDROCHLORIDE 10.5 g. of 1-(3,4-methylenedioxyphenyl)-2-nitroethanol are dissolved in 150 ml. of methanol and to the solution is added 1 g. of palladium carbon. The resulting mixture is hydrogenolyzed with vigorous stirring. After the absorption of hydrogen is complete, the stirring is discontinued and the catalyst is filtered off and the filtrate is concentrated to dryness. The residue is dissolved in ethyl acetate and ethyl acetate acidified with hydrochloric acid is added to the solution until the white turbidity ceases to form. The crystals which form on standing are filtered off and washed thoroughly with ethyl acetate. Upon recrystallization from isopropyl alcohol, 8.3 g. of 1-(3,4-methylenedioxyphenyl)-2-aminoethanol hydrochloride are obtained.

Melting point: 181°–182° C. Elementary analysis: as $C_9H_{11}NO_3.HCl$; Calculated: C=49.65, H=5.51, N=6.43; Found: C=49.73, H=5.57, N=6.32.

EXAMPLE B

α-ISOPROPYLAMINO-(3,4-METHYLENEDIOXY)ACETOPHENONE HYDROBROMIDE 10 g. of α-bromo-(3,4-methylenedioxy)acetophenone are dissolved in 100 ml. of ethyl acetate and to the solution are added dropwise with stirring 9 g. of isopropylamine at 3°–5° C. After completion of the dropwise addition, the stirring is continued for 30 minutes, and then the solvent and isopropylamine are removed under reduced pressure to obtain 8.9 g. of α-isopropylamino-(3,4-methylenedioxy)acetophenone hydrobromide having a melting point of 206°–208° C.

Elementary analysis: as $C_{12}H_{15}NO_3.HBr$; Calculated: C=47.70, H=5.34, N=4.64; Found: C=47.81, H=5.42, N=4.49.

The free amine is obtained by dissolving the salt in water and making the aqueous solution alkaline with an aqueous saturated solution of sodium hydrogen carbonate. The aqueous solution is extracted with chloroform to obtain α-isopropylamino-(3,4-methylenedioxy)acetophenone in its free form.

EXAMPLE C

α-ISOPROPYLAMINO-(3,4-METHYLENEDIOXY)ACETOPHENONE 50 g. of 4-(chloroacetyl)catechol are dissolved in 500 ml. of ethyl acetate and to the solution are added dropwise with stirring 45 g. of isopropylamine at 3°–5° C. After completion of the dropwise addition, the stirring is continued for 30 minutes. The solvent and isopropylamine are then removed under reduced pressure to obtain 42.5 g. of 4-(isopropylaminoacetyl)catechol hydrochloride.

Elementary analysis: as $C_{11}H_{15}NO_3.HCl$; Calculated: C=53.76, H=6.58, N=5.70; Found: C=53.82, H=6.61, N=5.66.

4-(isopropylaminoacetyl)catechol hydrochloride (34 g.) is dissolved in 60 ml. of water and the aqueous solution is made alkaline with an aqueous saturated sodium hydrogen carbonate solution. The resulting alkaline solution is extracted with chloroform. Upon removal of the chloroform by distillation, crude 4-(isopropylaminoacetyl)catechol is obtained. The crude product is purified by recrystallization from benzene-petroleum ether. 20.9 g. of 4-(isopropylaminoacetyl)catechol and 10.2 g. of methylene chloride are dissolved in 20 ml. of methanol and the resulting solution is placed in a glass pressure reactor together with 3 g. of Tobin bronze shavings. An additional 40 ml. of methanol are added to the solution and the reactor is cooled with ice. An ice cold aqueous KOH solution (consisting of 11 g. of KOH and 15 ml. of water) is added thereto dropwise with stirring and, after the addition is complete, the reactor is sealed. The reaction is carried out with stirring at 100°–110° C. for 18 hours. After the reaction is complete, the methanol is distilled of under reduced pressure. The residual aqueous alkaline solution is mixed with 100 ml. of water and then extracted with ether. The ether extract is washed with 1N KOH and water and then dried. Upon distillation of the ether, crude α-isopropylamino-(3,4-methylenedioxy)acetophenone is obtained. Upon recrystallization of the crude product from benzene-petroluem ether, 8.2 g. of crystalline α-isopropylamino-(3,4-methylenedioxy)acetophenone are obtained.

The crystalline α-isopropylamino-(3,4-methylenedioxy)acetophenone (8.2 g.) is dissolved in ethyl acetate, and ethyl acetate acidified with hydrobromic acid is added to the solution until the white turbidity ceases to form. The crystals which form on standing are filtered off and washed thoroughly with ethyl acetate. Upon recrystallization from isopropyl alcohol, 9.6 g. of α-isopropylamino-(3,4-methylenedioxy)acetophenone hydrobromide are obtained.

Melting point: 206°–208° C. Elementary analysis: as $C_{12}H_{15}NO_3.HBr$; Calculated: C=47.70, H=5.34, N=4.64; Found: C=47.67, H=5.32, N=4.66.

EXAMPLE D

α-ISOPROPYLBENZYLAMINO-(3,4-METHYLENEDIOXY)ACETOPHENONE HYDROCHLORIDE 50 g. of α-bromo-(3,4-methylenedioxy)acetophenone are dissolved in 700 ml. of ethyl acetate and to the solution are added dropwise with stirring 62.5 g. of isopropylbenzylamine at 3°–5° C. After completion of the dropwise addition, the stirring is continued for 30 minutes. Then the isopropylbenzylamine hydrobromide which separates out in the reaction mixture is filtered off. To the filtrate, ethyl acetate acidified with hydrochloric acid is added until the white turbidity ceases to form. The crystals which form on standing are filtered off and washed with ethyl acetate. Upon recrystallization from isopropyl alcohol, 52.5 g. of α-isopropylbenzylamino-(3,4-methylenedioxy)acetophenone hydrochloride are obtained.

Elementary analysis: as $C_{19}H_{21}NO_3.HCl$; Calculated: C=65.61, H=6.38, N=4.03; Found: C=65.58, H=6.36, N=4.07.

EXAMPLE E

1-(3,4-METHYLENEDIOXYPHENYL)-2-ISOPROPYLBENZYLAMINOETHANOL HYDROCHLORIDE 16.4 g. of (3,4-methylenedioxyphenyl)ethylene oxide are refluxed for 6 hours together with 75 g. of isopropylbenzylamine in 100 ml. of ethanol. After cooling, the ethanol and the excess amine are distilled off under reduced pressure. The residue is extracted with 100 ml. of 1N HCl and the extract is washed twice with 50 ml. of ether. The hydrochloric acid extract is made basic with 1N NaOH and the liberated oil is extracted with ether. After drying the extract, the product is crystallized out of solution as the hydrochloride by adding a hydrochloric acid-acidified ether solution to the dried ether extract. The crystals are isolated by filtration and upon drying, 17.9 g. of 1-(3,4-methylenedioxyphenyl)-2-isopropylbenzylaminoethanol hydrochloride are obtained.

Melting point: 163°–164° C. Elementary analysis: as $C_{19}H_{23}NO_3.HCl$; Calculated: C=65.23, H=6.91, N=4.00; Found: C=65.41, H=6.90, N=4.02.

EXAMPLE F

1-(3,4-METHYLENEDIOXYPHENYL)-2-ISOPROPYLBENZYLAMINOETHANOL HYDROCHLORIDE 20.5 g. of 1-(3,4-methylenedioxyphenyl)-2-chloroethanol are refluxed for 8 hours together with 75 g. of isopropylbenzylamine in 100 ml. of ethanol. After cooling the reaction mixture, the ethanol and the excess amine are distilled of under reduced pressure. The residue is extracted with 100 ml. of 1N HCl and the extract is washed twice with 50 ml. of ether. The hydrochloric acid extract is made alkaline with 1N NaOH and the oil which separates is extracted with ether. After drying the ether extract, the product is crystallized out of solution as the hydrochloride by adding an ether solution acidified with hydrochloric acid to the dry ether extract. The crystals are isolated by filtration and upon drying, 15.5 g. of 1-(3,4-methylenedioxyphenyl)-2-isopropylbenzylaminoethanol hydrochloride are obtained.

Melting point: 163°–164° C. Elementary analysis: as $C_{19}H_{23}NO_3.HCl$; Calculated: C=65.23, H=6.91, N=4.00; Found: C=65.29, H=7.20, N=4.19.

EXAMPLE G

1-(3,4-METHYLENEDIOXYPHENYL)-2-t-BUTYLBENZYLAMINOETHANOL HYDROCHLORIDE

The procedure described in Example F is repeated except that 87 g. of t-butylbenzylamine are used in place of the isopropylbenzylamine. 16.3 g of 1-(3,4-methylenedioxyphenyl)-2-t-butylbenzylaminoethanol hydrochloride are obtained.

Elementary analysis: as $C_{20}H_{25}NO_3 \cdot HCl$; Calculated: C=66.01, H=7.20, N=3.84; Found: C=65.97, H=7.23, N=3.80.

EXAMPLE H

α-(t-BUTYLBENZYLAMINO)-(3,4-METHYLENEDIOXY)ACETOPHENONE HYDROCHLORIDE

The procedure described in Example D is repeated except that 67.5 g. of t-butylbenzylamine are used in place of the isopropylbenzylamine. 56.5 g. of α-(t-butylbenzylamino)-(3,4-methylenedioxy)acetophenone hydrochloride are obtained.

Elementary analysis: as $C_{20}H_{23}NO_3 \cdot HCl$; Calculated: C=66.38, H=6.68, N=3.87; Found: C=66.41, H=6.65, N=3.84.

Figure 2:
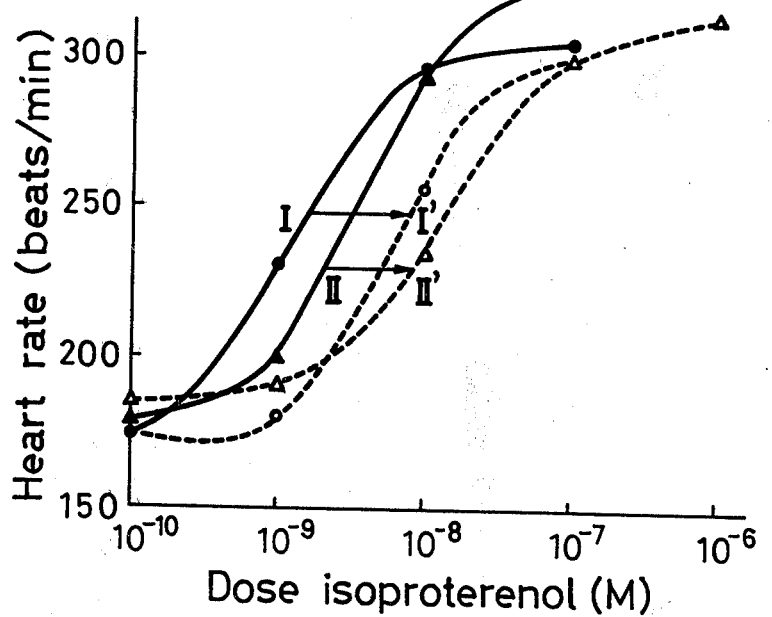

BETA-ADRENERGIC BLOCKING ACTIVITY OF 1-(3,4-METHYLENEDIOXYPHENYL)-2-ISOPROPYLAMINOETHANOL

β-Adrenergic blocking activity of the test compound, 1-(3,4-methylenedioxyphenyl)-2-isopropylaminoethanol, is studied of its effects on chronotropic response to isoproterenol in isolated guinea pig atrial preparations (Test 1) and inotropic responses to isoproterenol in a tracheal chain of guinea pigs (Test 2) and in a taenia coli of guinea pigs (Test 3). The results are respectively shown in FIGS. 1, 3 and 5. Experiments are also carried out using 1-(4-methylsulfonylaminophenyl)-2-isopropylaminoethanol as a control compound. The results are shown in FIGS. 2, 4 and 6. Experiments are carried out using Krebs-Ringer's organ bath in the absence and in the presence of the test compound or the control compound. Where either of the compounds is present, the concentration of the compound in the bath is $10^{-6}$g/ml. Effects of the test compound and the control compound are determined twice in Tests 1 and 2 while those are determined only once in Test 3. In the figures, Curves I and II show the dose-response relations in the absence of the test or control compound and corresponding Curves I' and II' show those in the presence of the compound.

1. EFFECT ON CHRONOTROPIC RESPONSE TO ISOPROTERENOL IN ISOLATED GUINEA PIG ATRIAL PREPARATION

Male guinea pigs weighing from 300 to 400 g. are killed by a blow on the head. Through a thoracic incision, the heart is quickly dissected out and freed from connective and adipose tissues in oxygenated Krebs-Ringer's solution. Both left and right atria are detached from ventricles. Each end of the atria is ligated with a cotton thread and mounted in 30 ml. Krebs-Ringer's organ bath gassed with 95% $O_2$ and 5% $CO_2$ and maintained at 37° C. The isometric contraction and heart rate are measured by means of a strain gauge transducer and a pulse rate tachometer, respectively. These are recorded on an ink-writing oscillograph. Effects of the test compound and the control compound on the dose-heart rate relations of the atrial preparation in response to isoproterenol are investigated. Since isoproterenol is cumulatively added to the organ bath, inotropic responses do not appear in a precise dose-dependent shape, and the dose-response curves are obtained from the chronotropic responses of the atria. The results are illustrated in FIGS. 1 and 2.

2. EFFECT ON INOTROPIC RESPONSE TO ISOPROTERENOL IN TRACHAEL CHAIN OF GUINEA PIGS

Whole trachea tube is excised from a male guinea pig and cut open longitudinally along the anterior side of the trachea. The opened trachea is cut transversely along the ring cartilage into strips of 1-2 mm. in width. Six of these strips are tied in series to form a tracheal chain. The trachael chain preparation is set up in Krebs-Ringer's organ bath gassed with 95% $O_2$ and 5% $CO_2$ and maintained at 37° C. The contraction and relaxation of the tracheal chain are isotonically recorded on an ink-writing kymograph. Isoproterenol is cumulatively applied to the tracheal chain which is in nearly maximum contraction induced by $2 \times 10^{-5}M$ histamine. Effects of the test compound and the control compound on the dose-relaxation relations of the trachea in response to isoproterenol are investigated. The results are shown in FIGS. 3 and 4.

3. EFFECT ON INOTROPIC RESPONSE TO ISOPROTERENOL IN TAENIA COLI OF GUINEA PIGS

A taenia coli is excised from a male guinea pig to have a length of about 2 cm. and suspended in Krebs-Ringer's organ bath. The bath fluid is maintained at 37° C. and gassed with 95% $O_2$ and 5% $CO_2$. The contraction and relaxation are recorded with an isotonic lever on a kymograph. Since the preparation spontaneously preserves certain tones, isoproterenol is cumulatively applied without any pre-treatment. Effects of the test compound and the control compound on the dose-relaxation relations of the taenia coli in response to isoproterenol are investigated. The results are shown in FIGS. 5 and 6.

From FIGS. 1 to 6, it is apparent that 1-(3,4-methylenedioxyphenyl)-2-isopropylaminoethanol has β-adrenergic blocking activity and that the activity is not significantly different from that of 1-(4-methylsulfonylaminophenyl)-2-isopropylaminoethanol.

What is claimed is:

1. A process for reducing blood pressure and blocking β-adrenergic receptor, which comprises the administration of an effective amount of a composition comprising as its active ingredient a 1-(3,4-methylenedioxyphenyl)-2-alkylaminoethanol compound represented by the formula:

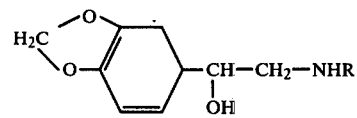

wherein R is an alkyl group having 2 to 6 carbon atoms, or a pharmaceutically acceptable acid addition salt thereof.

2. The process according to claim 1, wherein the active ingredient is 1-(3,4-methylenedioxyphenyl)-2-isopropylaminoethanol.

3. The process according to claim 1, wherein the active ingredient is 1-(3,4-methylenedioxyphenyl)-2-t-butylaminoethanol.

4. The process according to claim 1 wherein said active ingredient is in the form of a pharmaceutically acceptable acid addition salt selected from the group consisting of oxalate, lactate, tartrate, naphthoate, acetate, salicylate, citrate, benzoate, adipate, and maleate.

5. The process according to claim 1 wherein said active ingredient is in the form of a pharmaceutically acceptable acid addition salt selected from the group consisting of hydrochloride, hydrobromide, phosphate and sulfate.

6. The process according to claim 1 wherein said active ingredient is 1-(3,4-methylenedioxyphenyl)-2-isopropylaminoethanol hydrochloride.

7. The process according to claim 1 wherein said active ingredient is 1-(3,4-methylendioxyphenyl)-2-ethylaminethanol hydrochloride.

8. The process according to claim 1 wherein said active ingredient is 1-(3,4methylenedioxyphenyl)-2-t-butylaminoethanol hydrochloride.

* * * * *

UNITED STATES PATENT OFFICE
CERTIFICATE OF CORRECTION

Patent No. 4,147,799　　　　　　　　Dated April 3, 1979

Inventor(s) Hiroyuki Obase, et al.

It is certified that error appears in the above-identified patent and that said Letters Patent are hereby corrected as shown below:

Col. 2, line 66, "methylenedioxyyphenyl" should be --methylenedioxyphenyl--;

Col. 3, line 46, "$H_2HR$" should be --$H_2NR$--

Col. 6, line 14, "reactior" should be --reaction--;

line 46, "mol." should be --ml.--;

Col. 7, line 7, "Caliculated" should be --Calculated--;

Col. 8, line 43, "methyllenedioxyphenyl" should be --methylenedioxyphenyl--;

Col. 11, line 35, "of" should be --off--.

Signed and Sealed this

Seventeenth Day of July 1979

[SEAL]

Attest:

LUTRELLE F. PARKER

Attesting Officer　　Acting Commissioner of Patents and Trademarks